(12) United States Patent
Toner et al.

(10) Patent No.: US 8,343,756 B2
(45) Date of Patent: Jan. 1, 2013

(54) DEVICES AND METHODS FOR CELL MANIPULATION

(75) Inventors: Mehmet Toner, Wellesley, MA (US); Daniel Irimia, Charlestown, MA (US)

(73) Assignee: The General Hospital Corporation, Boston, MA (US)

( * ) Notice: Subject to any disclaimer, the term of this patent is extended or adjusted under 35 U.S.C. 154(b) by 954 days.

(21) Appl. No.: 12/089,440

(22) PCT Filed: Oct. 10, 2006

(86) PCT No.: PCT/US2006/039441
§ 371 (c)(1),
(2), (4) Date: Feb. 20, 2009

(87) PCT Pub. No.: WO2007/044690
PCT Pub. Date: Apr. 19, 2007

(65) Prior Publication Data
US 2009/0221073 A1    Sep. 3, 2009

Related U.S. Application Data

(60) Provisional application No. 60/724,453, filed on Oct. 7, 2005.

(51) Int. Cl.
C12M 1/02 (2006.01)
C12M 1/36 (2006.01)
C12M 1/34 (2006.01)

(52) U.S. Cl. .................................... 435/287.2

(58) Field of Classification Search ............... None
See application file for complete search history.

(56) References Cited

U.S. PATENT DOCUMENTS

| | | | |
|---|---|---|---|
| 6,168,948 B1 * | 1/2001 | Anderson et al. | 435/287.2 |
| 6,622,746 B2 | 9/2003 | Yang et al. | |
| 6,626,417 B2 * | 9/2003 | Winger et al. | 251/129.06 |
| 6,632,619 B1 * | 10/2003 | Harrison et al. | 435/7.2 |
| 6,644,944 B2 * | 11/2003 | Karp | 417/566 |
| 2003/0214057 A1 | 11/2003 | Huang | |
| 2007/0041878 A1 * | 2/2007 | Bryning et al. | 422/103 |

FOREIGN PATENT DOCUMENTS

GB    1264709    *    2/1972

OTHER PUBLICATIONS

Ahn et al., Proceedings of the IEEE, 2004, 92, pp. 54-173.
Alvarez et al., Human Reproduction, 1993, 8, pp. 1087-1092.
Andersson and Van Den Berg, Sensors and Actuators B-Chemical, 2003, 92, pp. 315-325.
Arai et al., Electrophoresis, 2001, 22, pp. 283-288.
Baek et al., Journal of Micromechanics and Microengineering, 2005, 15, pp. 1015-1020.
Columbus and Palmer, Clinical Chemistry, 1991,37, pp. 1548-1556.
Gascoyne and Vykoukal, Proceedings of the Ieee, 2004, 92, pp. 22-42.
Glasgow et al. Wheeler, IEEE Transactions on Biomedical Engineering, 2001, 48, pp. 570-578.
Grover et al., Sensors and Actuators B-Chemical, 2003 89, pp. 315-323.
Hansen et al., Proceedings of the National Academy of Sciences of the United States of America, 2002, 99, pp. 16531-16536.
Hosokawa and Maeda, Journal of Micromechanics and Microengineering, 2000, 10, pp. 415-420.
Irimia et al., Analytical Chemistry, 2004, 76, pp. 6137-6143.
Katkov and Mazur, Cell Biochemistry and Biophysics, 1999,31, pp. 231-245.
Leclerc et al., Biotechnology Progress, 2004, 20, pp. 750-755.
Li and Li, Analytical Chemistry, 2005, 77, pp. 4315-4322.
Li et al., Electrophoresis, 2005, 26, pp. 3758-3764.
Li et al., Lab on a Chip, 2004, 4, pp. 174-180.
Panaro et al., Biomolecular Engineering, 2005, 21, pp. 157-162.
Pugia et al., Clinical Chemistry, 2005, 51, pp. 1923-1932.
Randall and Doyle, Proceedings of the National Academy of Sciences of the United States of America, 2005, 102, pp. 10813-10818.
Rosenthal and Voldman, Biophysical Journal, 2005, 88, pp. 2193-2205.
Seger et al., Lab on a Chip, 2004, 4, pp. 148-151.
Sethu et al., Analytical Chemistry, 2004, 76, pp. 6247-6253.
Sia and Whitesides, Electrophoresis, 2003, 24, pp. 3563-3576.
Singh, Cytometry, 1998,31, pp. 229-232.
Srinivasan et al., Lab on a Chip, 2004, 4, pp. 310-315.
Stibenz and Buhrer, Scandinavian Journal of Immunology, 1994,39, pp. 59-63.
Studer et al., Journal of Applied Physics, 2004, 95, pp. 393-398.
Sundararajan et al., Lab on a Chip, 2005, 5, pp. 350-354.
Toner and Irimia, Annual Review of Biomedical Engineering, 2005, 7, pp. 77-103.
Tudos et al, Lab on a Chip, 2001, 1, pp. 83-95.
Unger et al., Science, 2000, 288, pp. 113-116.
Voldman et al., Biophysical Journal, 2001; 80, pp. 531-541.
Weibel et al., Analytical Chemistry, 2005, 77, pp. 4726-4733.
Wheeler et al., Analytical Chemistry, 2003, 75, pp. 3581-3586.
Yang et al., Analytical Chemistry, 2002, 74, pp. 3991-4001.

* cited by examiner

*Primary Examiner* — Joanne Hama
(74) *Attorney, Agent, or Firm* — Fish & Richardson P.C.

(57) ABSTRACT

Devices for fluid control and biological particle manipulation (e.g., cell enrichment and blood sampling) are disclosed. The devices a based on the ability to control the flow of fluids through the use of microfluidic valves. The valves are characterized, for example, by microstructures disposed on a mobile diaphragm.

3 Claims, 8 Drawing Sheets

DEVICES AND METHODS FOR CELL MANIPULATION

CROSS-REFERENCE TO RELATED APPLICATIONS

This application is the National Stage of International Application No. PCT/US2006/039441, filed Oct. 10, 2006, which claims benefit of U.S. Provisional Application No. 60/724,453, filed Oct. 7, 2005.

BACKGROUND OF THE INVENTION

The invention relates to the fields of cell enrichment, blood sampling, and microfluidic devices.

Lab-on-a-chip technologies for cell-based, basic scientific or clinical applications promise to integrate all procedures from primary sample collection to data analysis in small, inexpensive, and versatile devices (Andersson and Van Den Berg, Sensors and Actuators B-Chemical, 2003, 92, 315-325; Sia and Whitesides, Electrophoresis, 2003, 24, 3563-3576; Toner and Irimia, Annual Review of Biomedical Engineering, 2005, 7, 77-103). One step in this complex process is sample preparation, when cells from primary samples are typically separated, washed, and re-suspended in new buffer solutions, with or without specific stimulation steps, before they are made available for subsequent processing and analysis. However, most of the time this step is accomplished not on the chip but on the bench, by procedures like pipetting and centrifugation, because no common, easy-to-implement approaches exist today for on chip sample preparation.

Handling of mammalian cells in microfluidic devices poses some nontrivial challenges. Eukaryotic cells in general and human cells in particular are mechanically more fragile and more deformable than other cells. They are also biologically more sensitive and quicker to respond to changes in their environment. While various methods for handling cells in suspensions have been proposed, each technique has drawbacks that limit its potential. Methods using electric fields for trapping and exposing mammalian cells to new reagents (Rosenthal and Voldman, Biophysical Journal, 2005, 88, 2193-2205; Gascoyne and Vykoukal, Proceedings of the Ieee, 2004, 92, 22-42; Seger et al., Lab on a Chip, 2004, 4, 148-151) are dependent on the solution for cell suspension and on the cell type. Optical manipulation of relatively large mammalian cells (Arai et al., Electrophoresis, 2001, 22, 283-288) can be laborious and expensive and cannot be easily scaled up, while the use of mechanical structures (Panaro et al., Biomolecular Engineering, 2005, 21, 157-162; Wheeler et al., Analytical Chemistry, 2003, 75, 3581-3586; Glasgow et al. Wheeler, Ieee Transactions on Biomedical Engineering, 2001, 48, 570-578) is usually irreversible, since once cells are mechanically trapped they cannot be easily released.

Precise metering of whole blood samples is essential for many clinical diagnostic applications, e.g., the biochemical analysis of blood (Tudos et al., Lab on a Chip, 2001, 1, 83-95) and blood cell counting and analysis (Toner and Irimia, Annual Review of Biomedical Engineering, 2005, 7, 77-103). Volumes of blood as small as a few microliters can be precisely sampled using syringes and micropipettes. However, smaller volumes, like those used in microfabricated devices require different approaches not always suited to complex cell-rich fluids like blood. Vented capillaries with a hydrophobic barrier (Pugia et al., Clinical Chemistry, 2005, 51, 1923-1932; Ahn et al., Proceedings of the Ieee, 2004, 92, 154-173; Columbus and Palmer, Clinical Chemistry, 1991, 37, 1548-1556) could trap air bubbles between fluid segments that need to be mixed. Microdroplets on electrowetting platforms (Srinivasan et al., Lab on a Chip, 2004, 4, 310-315) have to be formed outside the device by pipetting; their minimum size is limited to the microliter range, and stickiness of blood proteins and cells on the hydrophobic surfaces may be problematic. Finally, valves have been designed to sample sub-microliter volumes of fluid and perform biochemical assays (Hansen et al., Proceedings of the National Academy of Sciences of the United States of America, 2002, 99, 16531-16536), although the geometry of the valves is not friendly for cells. Precise metering volumes are possible using valves in channels with vertical walls (Li et al., Electrophoresis, 2005, 26, 3758-3764).

Thus, there is a need for new devices and methods for manipulating samples in microfluidic devices.

SUMMARY OF THE INVENTION

The invention features a microfluidic device including a channel and a valve. The valve has an open state allowing fluid flow through the channel, a first closed state resulting in the formation of a first chamber in the channel, and a second closed state resulting in the formation of a second chamber in the channel. The invention also includes a method of using the above device.

The invention also features a method of trapping a fluid or a biological particle (e.g., a mammalian cell), introducing a fluid or a fluid containing a biological particle into a microfluidic device including a channel and a valve. In this embodiment the valve has an open state allowing the fluid to flow through the channel, a first closed state resulting in the formation of a first chamber in the channel, and a second closed state resulting in the formation of a second chamber in the channel.

In any of the devices of the invention, the valve can include a mobile diaphragm, microstructures, and a base member. In these devices, actuation of the mobile diaphragm results in movement of at least a portion of the microstructures relative to the base member or the mobile diaphragm relative to at least a portion of the microstructures, resulting in the formation of the first chamber or the second chamber. Combinations of these methods of actuation are also possible.

At least a portion of the microstructures can be disposed on the mobile diaphragm in any of the devices of the invention. In these devices, the actuation of the mobile diaphragm results in movement of at least a portion of the microstructures relative to the base member. Also, at least a portion of the microstructures can be disposed on the base member. In these devices, the actuation of the mobile diaphragm results in movement of the mobile diaphragm relative to at least a portion of the microstructures. The microstructures can be of a height less than the height of the channel in any of the above devices.

The actuation of the mobile diaphragm of the above devices may, or may not, result in a seal being formed between at least a portion of the microstructures and either the mobile diaphragm or the base member. The first chamber or the second chamber of the device can separate one fluid from a second fluid.

The first or second closed state can trap particles but allows fluid to flow through the channel.

By "biological particle" is meant any species of biological origin that is insoluble in aqueous media on the time scale of sample acquisition, preparation, storage, and analysis. Examples include cells (e.g., animal cells, plant cells, bacteria, and yeast), particulate cell components, viruses, and complexes including proteins, lipids, nucleic acids, and carbohydrates.

By "chamber" is meant a volume of a microfluidic device separated from another volume of a microfluidic device so that passage of material between the two volumes is constrained. The term chamber is meant to include a partial separation (e.g., where cells or other particles cannot pass between the two volumes, but fluid can pass between the two volumes).

By "channel" is meant a gap through which fluid may flow. A channel may be a capillary, a conduit, or a strip of hydrophilic pattern on an otherwise hydrophobic surface wherein aqueous fluids are confined.

By "microfluidic" is meant having at least one dimension of less than 1 mm.

By "microstructure" is meant an impediment to flow in a channel, e.g., a protrusion from one surface.

By "trapping a biological particle" is meant the restricting a biological particle to a desired chamber.

By "valve" is meant a structure that controls the flow of a fluid. The term valve includes partial control of a fluid, whereby certain elements in the fluid are prevented from flowing, while other elements are permitted to flow (for example based upon size).

Other features and advantages will be apparent from the following description and the claims.

BRIEF DESCRIPTION OF THE DRAWINGS

FIG. 3D shows the valve in the closed position. FIG. 3E shows the valve in the open position.

FIGS. 4C and 4D demonstrate the handling of 30 nL of whole blood.

DETAILED DESCRIPTION OF THE INVENTION

In general, the invention features a microfluidic device containing a channel and a valve. The valve of the invention contains a mobile diaphragm and a base member. Actuation of the mobile diaphragm results in the relative movement of microstructures in the channel leading to the creation or destruction of chambers. In one example, the microstructures are disposed on the mobile diaphragm such that actuation of the diaphragm results in the microstructures forming chambers against a planar base member. Alternatively, the microstructures can be disposed on the base member, where actuation of a planar mobile diaphragm results in the microstructures forming chambers against the mobile diaphragm. Also, microstructures may also be disposed on both the mobile diaphragm and the base member.

No particular geometric arrangement of the mobile diaphragm and the base member is required, except that actuation of the diaphragm cause the creation or destruction of chambers. Typically, the diaphragm and base member will be disposed opposite and parallel to one another. However, other arrangements are possible, e.g., the angle between the mobile diaphragm and base member can be between 0 (inclusive) and 180 degrees (inclusive). In one embodiment, the invention also includes a nonplanar, e.g., curved, mobile diaphragm or base member.

Figure 1:
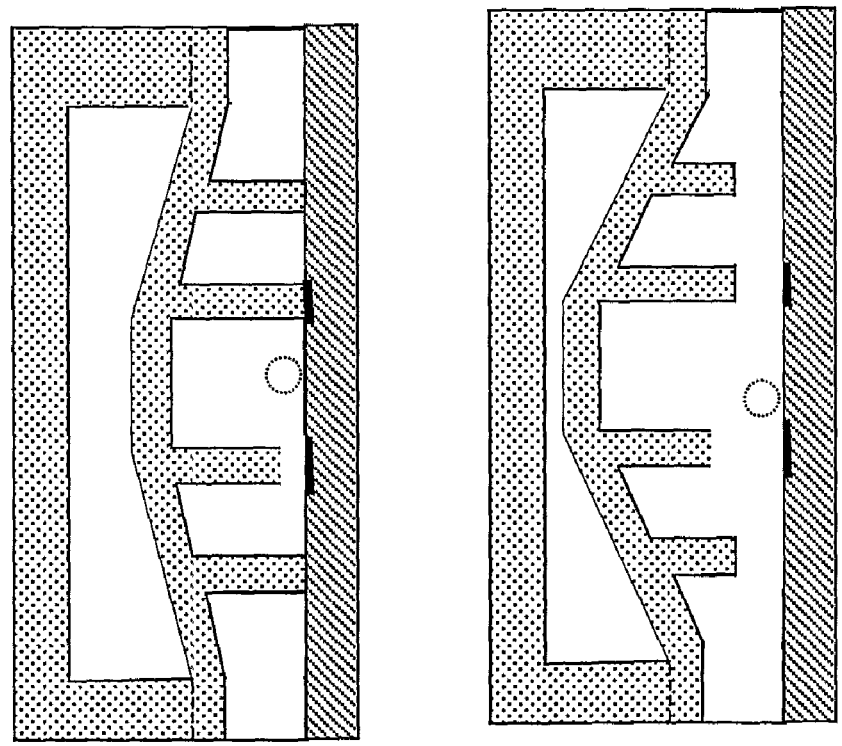
FIG. 1 is a set of schematics showing a valve where the height of microstructure disposed onto the mobile diaphragm is greater than the height of the channel.

When forming a chamber, the microstructures act with the base member and the channel as a whole to create a volume where passage of at least a portion of a fluid sample is constrained. The height of the microstructures used to create a chamber can be less than, equal to, or greater than (FIG. 1) the height of the channel to which they are connected. An important feature of the invention is that when the valve is closed, microstructure may, or may not, form a seal with the base member. For example, a chamber may be formed that excludes passage of fluid between the inside and outside of the chamber, or a chamber may be formed that allows fluid to pass but prevents particulate matter, e.g., above a desired size (e.g., from 0.1 μm to 1 mm ($10^{-7}$ to $10^{-3}$ m)), from entering or exiting a chamber. This embodiment of the invention can be used, for example, to trap a cell while permitting fluid to flow between two chambers.

The microstructures of the invention can form chambers of any shape (e.g., cylindrical, toroidal, spherical, rectangular, trapezoidal, or pyramidal). The thickness of the walls of the chamber will be determined, at least in part, by the thickness of the microstructures. The chambers formed by the actuation of the valves of the invention can be concentric or contiguous with each other.

Actuation of the mobile diaphragm is desirably accomplished pneumatically. Typically, a control channel is located adjacent to the mobile diaphragm. Increasing or decreasing the pressure in the control channel, relative to that in the channel in which the chambers form, causes the diaphragm to move. The diaphragm and microstructures may be designed so that formation of multiple chambers can be accomplished step-wise, i.e., different pressure differentials in the control chamber result in formation of different chambers, or simultaneously. The actuation of the mobile diaphragm of the invention can be used to create 1, 2, 3, 4, 10 or any number of chambers in a channel. Other methods for actuating a diaphragm are known in the art. For example, the diaphragm may be coupled to a manual or computer controlled piston capable of inducing the diaphragm to move relative to the base member. In other embodiments, the diaphragm may be actuated by electrical field, magnetic field, heat, light, or pH.

When reversible actuation of the mobile diaphragm is desired, an elastomeric or otherwise malleable material is employed. Examples include silicones and other polymeric elastomers. In certain embodiments, malleable metals or shape memory alloys may also be employed. When irreversible actuation is desired, materials that do not or do not easily return to a previous shape may be employed. The microstructures and the base member may be fabricated in any suitable material, as are commonly known in the microfluidics field. Examples include silicon, glass, metals, and other polymers. Combinations of materials may also be employed, e.g., a rigid material with an elastomeric coating to ensure a fluid tight seal. Materials employed may, or may not, be porous or selectively permeable. For example, microstructures or other components of the device may allow for fluid, e.g., gas or liquid exchange, or for chemical agent exchange, e.g., ions, drugs, etc. Reagents or other materials may also be dissolved, suspended, coated, or otherwise associated with the microstructures, base member, diaphgram, or other parts of the device. Such reagents may secrete into a chamber, e.g., during an assay, or react with components in the fluid in the chamber, e.g., to buffer pH, absorb waste by-products, or provide anchor sites for attachment. Microstructures may also be fabricated out of materials that disintegrate over time, e.g., to release the contents of a chamber after a desired amount of time, or disintegrate only after user intervention, e.g., raising temperature above the glass transition or decomposition temperature, dissolving in a solvent, or electrical breakdown or electrochemical degradation.

Methods for manufacturing microfluidic devices are known in the art. The exact methods employed will depend in part on the material used to manufacture the device. Typical techniques include photolithography, wet or dry chemical etching, electroforming, and molding. Exemplary manufacturing techniques are described herein.

Figure 2:
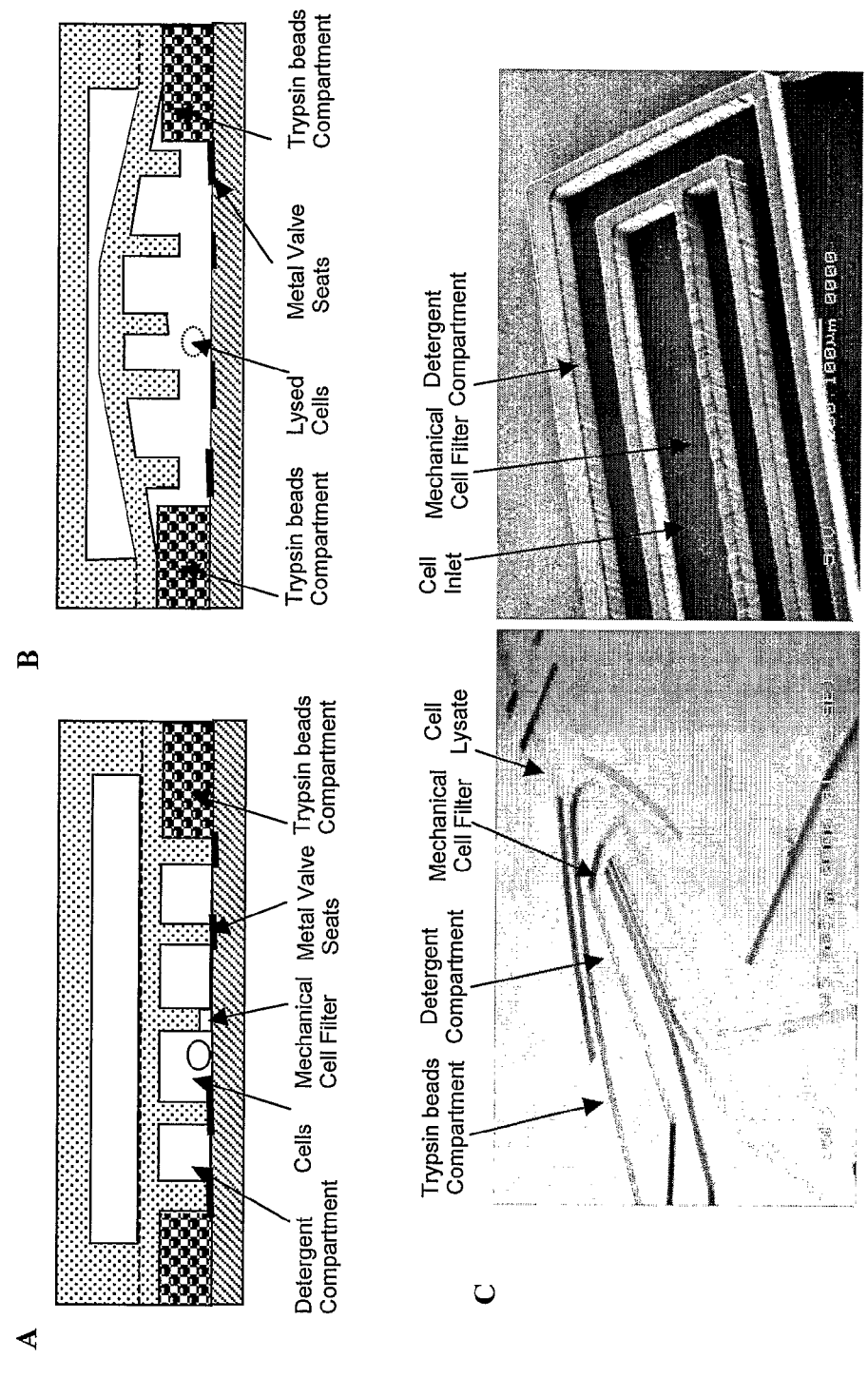
FIGS. 2A and 2B are schematics of a functioning cell lysis chamber using a microstructured diaphragm.
FIG. 2C is a set of photomicrographs of the functioning lysis chamber.
FIG. 2D is a set of schematics of a functioning device with microstructures on both the mobile diaphragm and base member.
FIG. 2E is a photomicrograph of a functioning device with microstructures on both the mobile diaphragm and base member.
Figure 2:
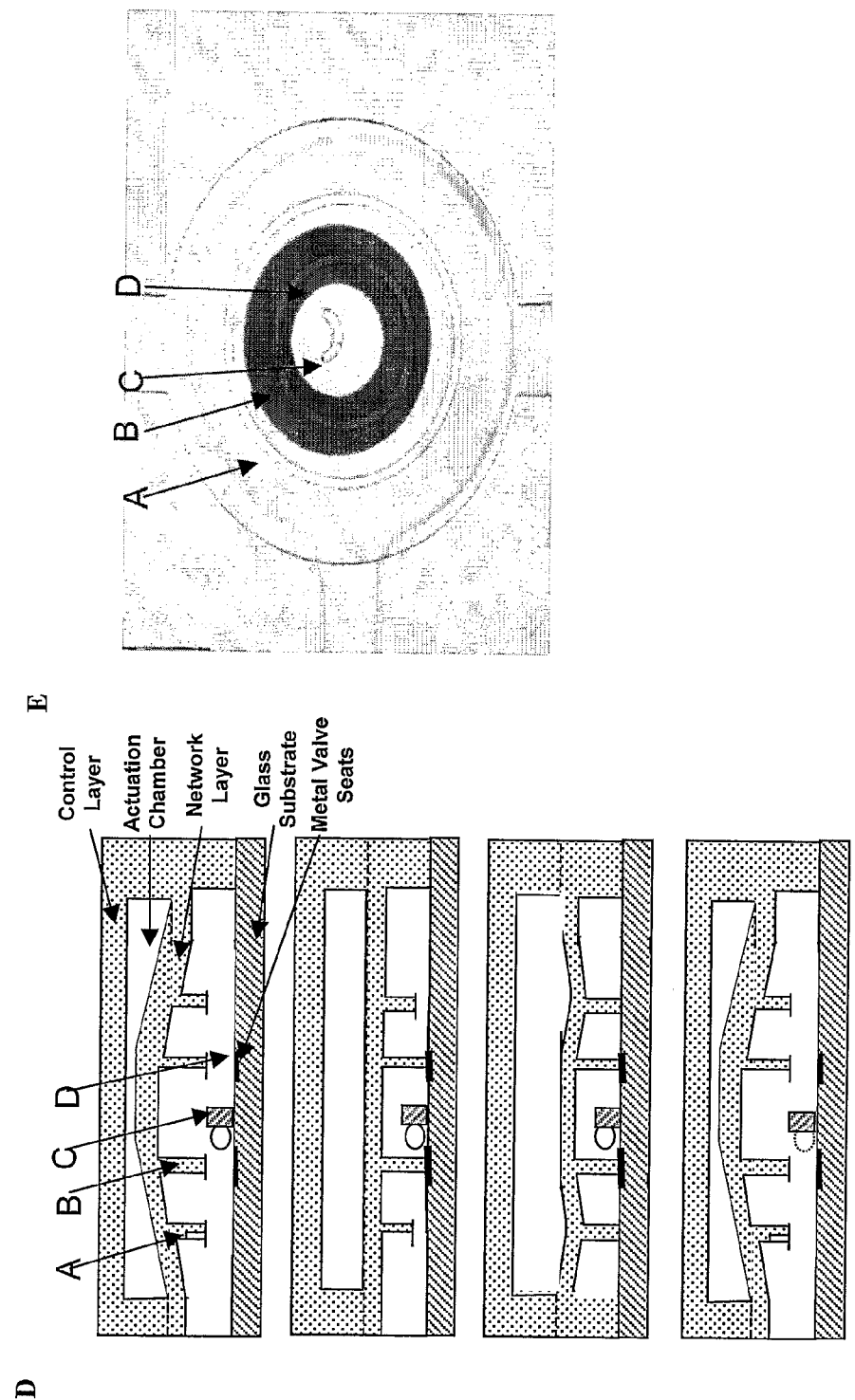

As one example, the invention features a normally closed pneumatic valve (FIGS. 2A and 2C). This valve is constructed by the controlling the sealing of PDMS and glass using a thin film metal layer. Other mechanisms for avoiding the sealing of the membrane to the bottom layer can be used. These include holding the microstructures at some distance from the bottom by applying suction to the control chamber and deforming the membrane, using a pattern of soluble material that could be removed after bonding, deactivation of the surfaces that will come into contact with each other, or any other non-removable material preventing sticking of the microstructures to the opposing member (e.g. photoresist, photoepoxy, and gel). The bottom of the membrane structure may be separated from glass by a thin (50 Å) layer of metal (e.g., chromium or gold) in the corresponding contact regions (FIGS. 2B and 2C). The remaining PDMS binds to the glass and forms conventional channels and chambers. In an additional embodiment of the invention, microstructures disposed on the mobile diaphragm can be used in combination with microstructures disposed onto the base member (FIGS. 2D and 2E).

Devices of the invention may be used for the manipulation and analysis of cells, fluids, and other analytes. The valves of the invention may reversibly decouple the flow of fluids and the displacement of particles, e.g., cells in suspensions for lab-on-a-chip applications. By using the microstructures on mobile diaphragms, the invention features precise control over the location of particles of interest, and new capabilities for controlling fluid and cell suspension flow. Exemplary devices of the invention include devices for blood sampling, cell enrichment, and sequential cell stimulation applications. In addition, the devices of the invention may be employed whenever controlled contacting of two or more fluids is desired.

The invention will now be described with reference to specific, non-limiting examples of its design, manufacture, and use.

EXAMPLE 1

Basic Device

Figure 3:
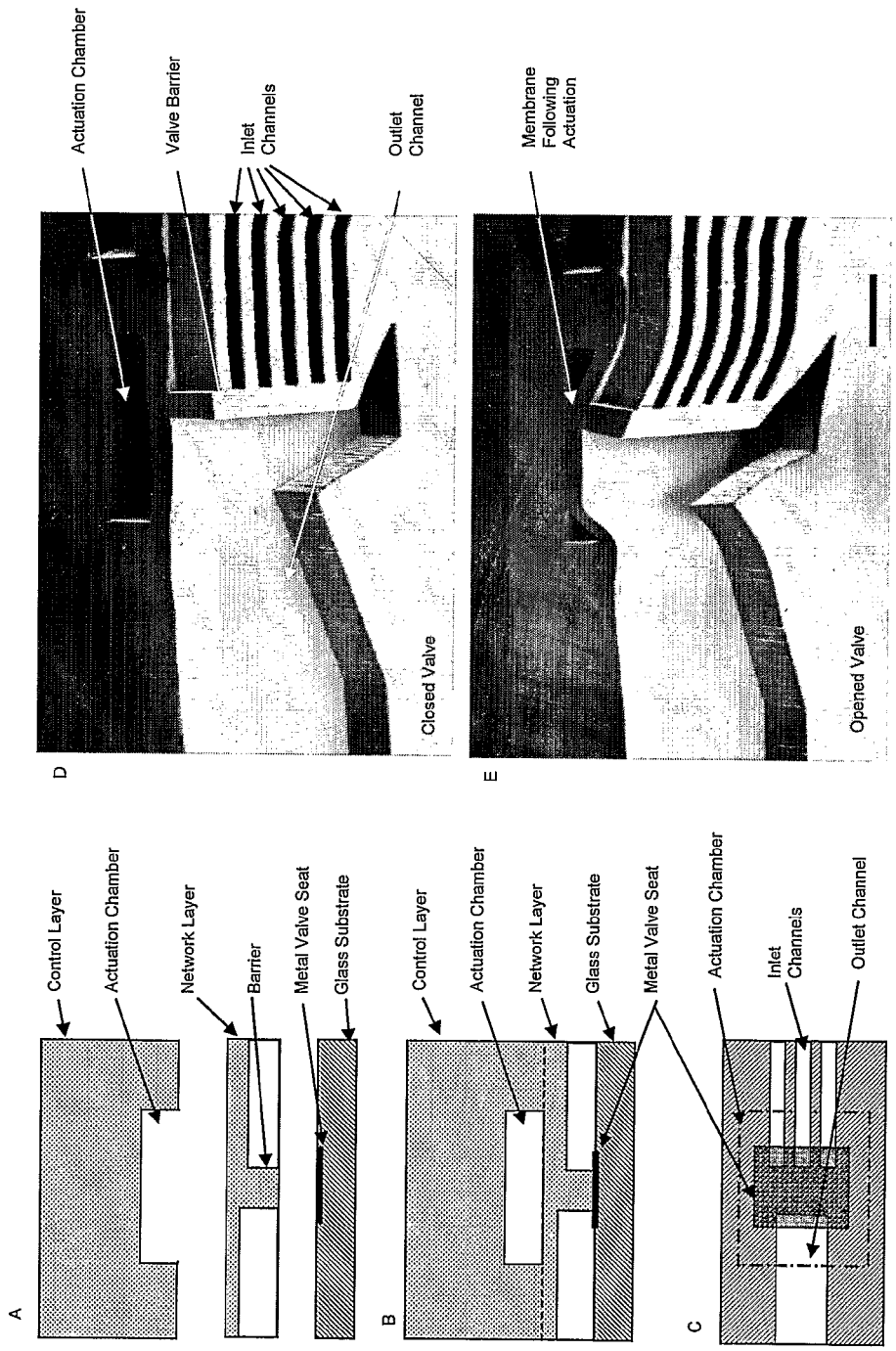
FIG. 3A is a schematic showing fabrication of the device.
FIGS. 3B and 3C are schematics showing side and top view of the assembled device.
FIGS. 3D and 3E are photomicrographs from a scanning electron microscope of a microstructured diaphragm functioning as a valve with multiple inlets and one outlet.

One embodiment of the invention features a two-layer PDMS device on glass, that incorporates a microfluidic network and a control layer, e.g., for handling small populations of suspended cells for sample preparation type applications (FIG. 3A). The two layers of PDMS were fabricated by casting the elastomer on separate photopatterned epoxy molds. The top, control layer contained a number of channels and the actuation chambers for the pneumatic valves. The bottom network layer contained the circuitry of channels of different widths and heights for the manipulation of cells and fluids. The control and network layers were bonded together and a membrane was formed between the actuation chambers in the top control layer and the bottom network layer (FIG. 3B). The two-layer construct was then selectively bonded on the top of a glass slide. The microstructures on the diaphragm were aligned to thin film metal patterns preventing the adhesion of the microstructure to the glass substrate (FIG. 3C). At the same time, the rest of the device was irreversibly bonded to unprotected glass. In the simplest configuration, the fluid flow in a system of channels in the network layer was controlled by the transversal microstructure on a membrane. In inactive position, the transversal structure rested on the metal pattern and separated the single or multiple inlet channels from the outlet channel (FIG. 3D). Upon actuation, the transversal structure was lifted by the upward deformation of the membrane into the control channel, allowing the simultaneous opening of the inlet channels into the outlet channel (FIG. 3E). The excursion of the membrane was large enough to allow passage of any object up to 50 μm in size, either particles or cells, and larger displacements are possible by increasing the thickness of the control channel.

Photoresist Molds

Two separate molds were prepared on silicon wafers using standard photolithography techniques. The mold for the control channels used one 50 μm thickness layer of SU8 epoxy (Microlithography Corp., Newton, Mass.), photopatterned through a mylar mask (Fineline Imaging, Colorado Springs, Colo.) and processed according to the manufacturer's specifications. The mold for the fluidic network layer used either one layer (30 μm) or two layers (3 and 30 μm) of SU-8 epoxy. The single layer was photopatterned on a silicon wafer, using the same protocol as the control layer. When two layers were employed, the thin layer was processed first and then the thicker layer was aligned and exposed under similar conditions on top of the first one. Small errors in mask alignment for the two layers could be tolerated by designing the masks such that smaller and larger structures were extended and partially overlapped.

Glass slides (45×50×0.1 mm; Fisher Scientific, Pittsburgh, Pa.) were sputtered with chrome (50 Å; Lance Goddard Associates, Foster City, Calif.). Subsequently, the thin metal film was patterned using standard microfabrication techniques. At the end, the glass slides were diced into smaller slides using a glass scriber.

Device Assembly

Poly(dimethyl siloxane) (PDMS, Sylgard 184; Dow Corning, Midland, Mich.) was prepared according to the manufacturer's instructions. To create complementary microchannels in PDMS, a 4 mm thick layer, and separately a 100 μm layer were cast over the control and network molds, respectively. The thickness of the network layer was controlled by spinning PDMS on the network mold at 500 rpm for 40 seconds. Holes were punched through the control layer using a sharpened 25-gauge needle (NE251PL, Small Parts Inc, Miami Lakes, Fla.). The two PDMS layers were exposed to oxygen plasma (50 W, 2% $O_2$, 25 seconds) in a parallel plate plasma asher (March Inc., Concord, Calif.) and bonded after contact and heating (75° C., 5 min). Through holes, defining the inlets and outlets for the network layer were subsequently punched using the same needle size. The bonding surfaces of the PDMS and the glass slides were treated with oxygen plasma. Precise alignment between the PDMS and the thin film metal patterns on the slides was achieved under a stereomicroscope (Leica MZ8, Leica, Heerbrugg, Switzerland). After the assembly of the device, the metal patch could be optionally removed using metal etchant solutions, to allow unobstructed view of the whole channel through the transparency of the glass or polymer. Extensive washing with distilled water from a syringe was employed to remove traces of the etching solution and avoid toxic effects on cells.

Tygon tubing (TGY-010, Small Parts) was inserted in the inlet and outlet holes and connected through blunt syringe needles (NE301PL, Small Parts) to fluid reservoirs (network channels) or 1 mL syringes (control channels). Pressure changes in the control channels were accomplished by manual displacement of the syringe plunger.

Cell Preparation

Human monocytic leukemia cells (THP-1, American Type Culture Collection, Manassas, Va.) were cultured in RPMI media (Invitrogen, Carlsbad, Calif.) supplemented with 10% fetal bovine serum (Invitrogen), 1 mM sodium pyruvate (Sigma Aldrich, St. Louis, Mo.) and 50 nM mercaptoethanol (Sigma Aldrich). Cells from the culture were centrifuged and resuspended in phosphate buffered solution (PBS, Invitrogen) to a concentration of $10 \times 10^6$ cells/mL. Several dilutions were prepared in the range $10^3$ to $10^7$ cells/mL by the addition of PBS to aliquots of the original suspension. Capillary blood was collected after pricking the skin of the middle finger of a healthy volunteer, and a volume up to 10 μL placed at the inlet of the device.

EXAMPLE 2

Sampling Precise Volumes from Cell Suspensions

Figure 4:
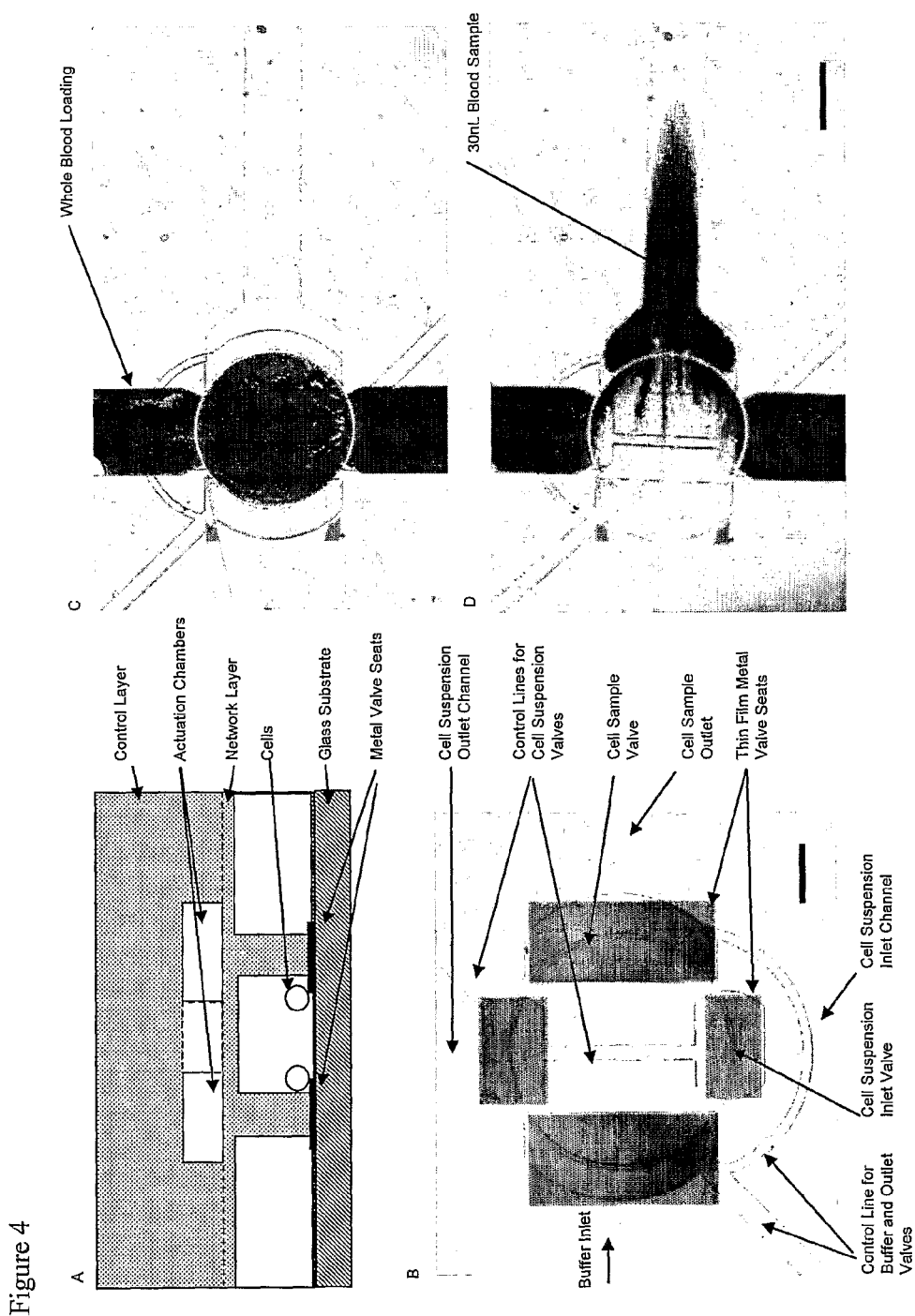
FIG. 4A is a schematic showing pairs of barriers used to sequester cells.
FIGS. 4B-4D are photomicrographs of the device.

Four barriers on separate membranes were combined to realize a T-junction type structure for sampling precise volumes from cell suspensions (e.g. whole blood). Two valves, their control chambers coupled, control the flow of the cell suspension along the vertical axis (FIG. 4A). A second pair of valves allowed the displacement of the precisely metered sample by flow of buffer along the horizontal axis into the outlet sampling channel (FIG. 4B). The microstructures on the valves, in the form of curved barriers defined the walls of a cylindrical chamber with a 30 nL volume (FIG. 4C). Repeated metering of whole blood was accomplished on the device by alternately operating the valves. The precision of the metering was verified by the absence of resident cells in the sampling chamber after the buffer wash (FIG. 4D).

The use of microstructured diaphragm for the implementation of four valves, in a chromatography T-junction-like design allowed the precise metering of 30 nL of blood. Chambers with volumes from a few nanoliters to several microliters were designed by changing the position of the microstructures or by altering the height of the chamber. Because of the efficient removal of all blood cells from the chamber after a sample, volumes of blood equal to multiples of the chamber volume could also be precisely metered. To accomplish this, repetitive, alternative opening and closing of the valves controlling the blood and the buffer can be used to load and unload the chamber.

Microstructured sieves can be quickly regenerated by the actuation of the supporting membrane and were implemented for controlled cell trapping and release. The new cell enrichment procedure was extremely effective for very low original cell concentrations when enrichment of three orders of magnitude was easily achieved. In addition, the device could efficiently handle very small samples, a situation when centrifugation would be ineffectual due to major cells losses while removing the supernatant. Such capabilities would be useful in microfluidic devices that are very likely to dilute the cell suspension by the addition of reagents and when the reconstitution of the initial cell concentration is important for later analysis. For example, selective destruction of cells in a blood sample during the preparation of the buffy-coat equivalent usually results in large-volume, low-cell concentration samples (Sethu et al., Analytical Chemistry, 2004, 76, 6247-6253). Subsequent cell analysis protocols would benefit from reducing the sample volume and increasing the cell concentration. In addition, on-chip processing is gentler and less likely to affect the cells of interest by exposure to mechanical stresses during centrifugation (Stibenz and Buhrer, Scandinavian Journal of Immunology, 1994, 39, 59-63; Alvarez et al., Human Reproduction, 1993, 8, 1087-1092; Katkov and Mazur, Cell Biochemistry and Biophysics, 1999, 31, 231-245). The new cell enrichment procedure may also be useful for the isolation of cells from dissociated tissues and removal of debris (Singh, Cytometry, 1998, 31, 229-232), or for separating particles cells based on size, in an approach comparable to mechanical filtering of blood cells (Toner and Irimia, Annual Review of Biomedical Engineering, 2005, 7, 77-103).

EXAMPLE 3

Cell Isolation

Figure 5:
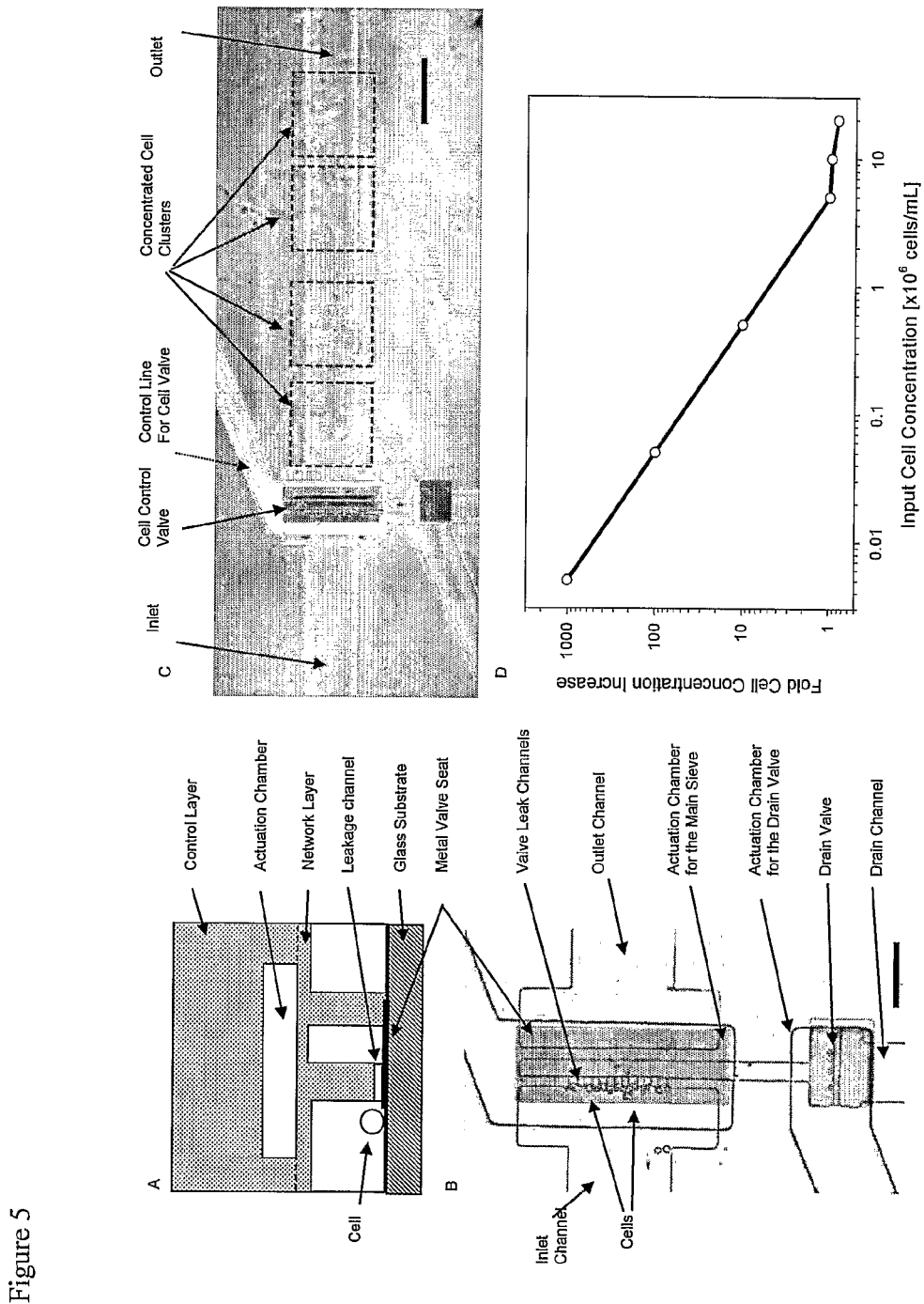
FIG. 5A is a schematic of a diaphragm combining two different microstructures: a barrier with small leak channels and a fall barrier.
FIGS. 5B and 5C are photomicrographs showing cell trapping.
FIG. 5D is a graph showing cell enrichment.
FIG. 5E is a three dimensional schematic of the microstructured diaphragm for cell pre-concentration in lab-on-a-chip devices.
FIG. 5F is a set of schematics showing a functioning cell concentrator.
Figure 5:
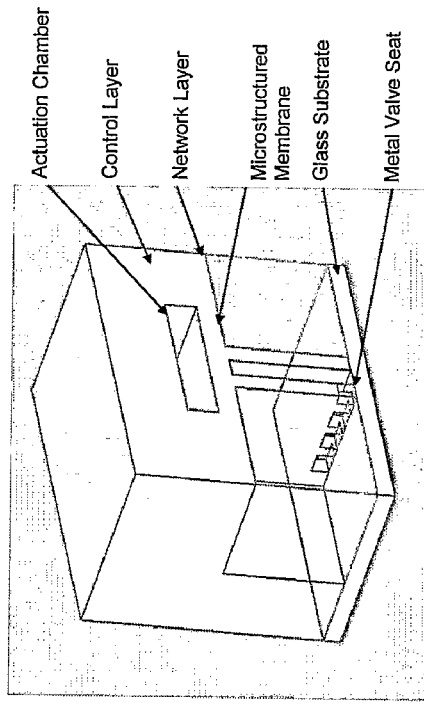
Figure 5:
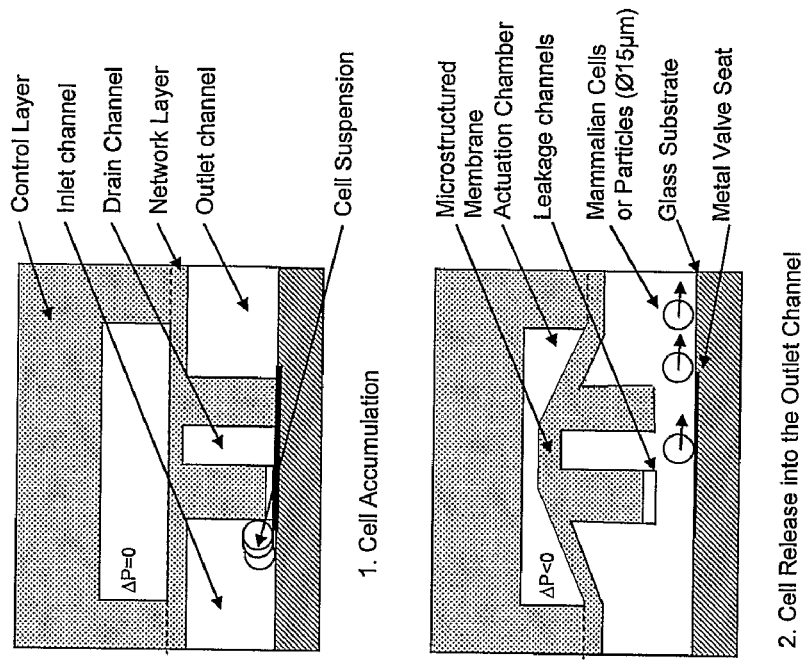

Several microstructures were combined on the same membrane for partial decoupling of cell movement and fluid flow. Two structures of different heights on the same membrane were used for concentrating a cell suspension, by splitting the liquid and the cells into distinct chambers (FIGS. 5A, 5E, and 5F). A first, leaky barrier, in resting position, allowed only the passage of fluid through 3×10 μm channels while mechanically blocking the cells. A second, fall barrier directed the leaked fluid into a drain channel. An additional microstructured diaphragm valve was used to control the flow in the drain channel independently (FIG. 5B). A cell suspension was introduced through the inlet channel, and cells were trapped at the leaky barrier. With the accumulation of cells at the first barrier, the flow was obstructed, because of the blocking of the small leaky channels. The accumulated cells were then transported into the outlet channel by briefly lifting and then quickly releasing the microstructured diaphragm. Clusters of enriched cells were directed into the outlet channel (FIG. 5C) and the sieve was regenerated and ready to capture more cells. To avoid the waste of captured cells into the drain channel, the drain valve was closed during this step. Through this procedure, the density of a sparse cell suspension could be increased in the output channel by several orders of magnitude. Cell suspensions with concentrations ranging from $1\times10^3$ to $1\times10^7$ cells/mL were enriched to $1\times10^7$ cells/mL. The concentration increase was more dramatic, up to three orders of magnitude, in the case of sparse cell suspensions (FIG. 5D). With increasing concentration of the cell suspension, an increasing number of cells are trapped in the 30 μm space between the first and second microstructured barriers and wasted into the drain channel, limiting the yield of enrichment for cell suspensions above $1\times10^7$ cells/mL. For low concentration suspensions, the limiting factor for enrichment was the time required for draining the suspension liquid and trapping the maximum number of cells at the first barrier.

EXAMPLE 4

Chemical Stimulation of Cells

Figure 6:
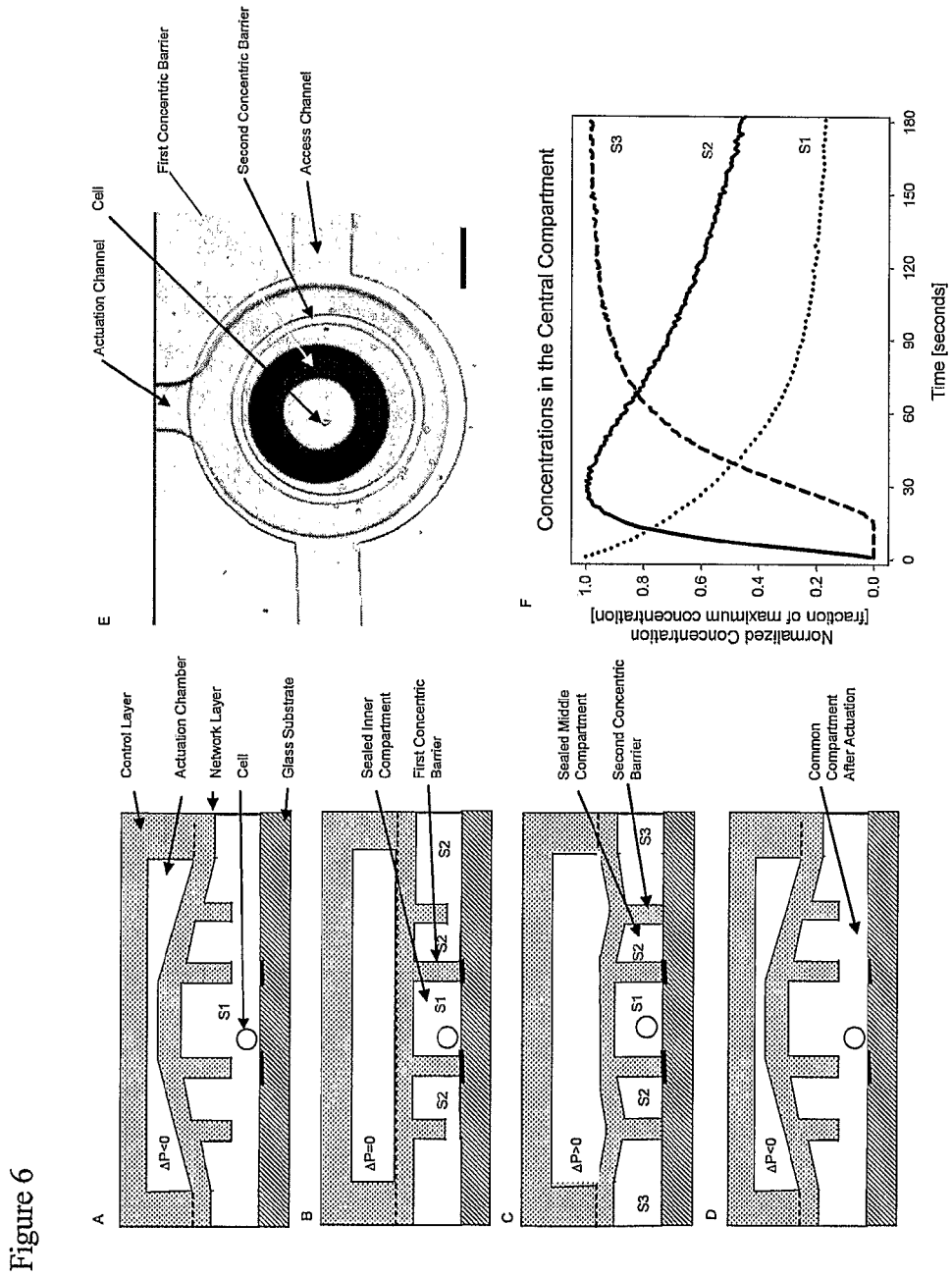
FIGS. 6A-6D are schematics showing circular ridges of different heights used to sequentially trap a cell in medium S1 in the central compartment and solution S2 in the middle compartment.
FIG. 6E is a photomicrograph of the microstructured diaphragm with circular ridges.
FIG. 6F is a graph showing the changes of relative concentrations in the center compartment as a function of time.

One cell was exposed to a fast temporal sequence of chemicals. A microstructured membrane with two concentric structures was employed to trap the cells and the reagents in a configuration that allowed the rapid exchange of solutions around the cell (FIGS. 6A-D). While the inner microstructure was the same height as the inlet channel, the outer one was shorter and could only touch the bottom glass when moderate pressure was applied through the control channel, and the membrane deformed downwards (FIG. 6C). The two concentric structures divided the chamber under the membrane into three distinct compartments. The inner compartment (S1) was the compartment where cells were trapped at the beginning of the experiment in their original suspension fluid. The middle compartment (S2) formed a ring around the inner compartment and was filled with the first solution of the sequence. The outer compartment (S3) was filled with the second solution of the temporal sequence. To load the device, the membrane was lifted by decreasing the pressure in the control channel, and a cell suspension was introduced (FIG. 6A). One cell was trapped in the inner compartment (S1) by venting the control chamber and relaxing the membrane (FIG. 6B). Subsequently, the first reagent was introduced, filling the middle and outer compartments. The middle compartment was then isolated by pushing down the membrane and was sealed between the two concentric structures (FIG. 6C). The device was completely loaded after the filling of the outer compartment with the second reagent (FIG. 6E). Perfect sealing was conveniently available for as long as needed, before sequential mixing was accomplished at the time of choice by lifting the membrane (FIG. 6D). The change of concentrations of solutions in the compartments over time, estimated from the quantified total fluorescence, is presented in FIG. 6F. We observed an initial exponential decay for the concentration in the inner compartment (S1), that reached an equilibrium level consistent with the dilution in the larger, limited space under the structured membrane. We also measured an initial fast increase, over approximately 30 sec, followed by slower decrease of the first reagent (S2) at the level of the cell in the inner compartment. The fast concentration increase was consistent with a cumulative effect of diffusion and convection from the middle compartment, while the slow decay was representative for diffusion-driven mixing. We recorded a 15 seconds delay in the increase of concentration at the cell level of the reagent from the outer compartment (S3). The concentration increase was slower than for S2, but still faster than expected by diffusion alone, suggesting at least a brief convective process immediately following the actuation. The axisymmetric configuration of the system assured that a cell in the middle of the inner compartment was exposed only to a temporal gradient, in the absence of a spatial gradient around the cell. We estimated less than 1% deviations from uniform conditions occurred on the circumference of a 20 μm diameter cell during exposure after loading the intermediate compartment with fluorescein solution and lifting the microstructured membrane.

The study of cellular responses to chemical stimulation is of fundamental importance for many biology studies. While macroscopic techniques using pipettes and Petri dishes are still widely used in biology labs, there is increasing interest for the more precise methods available through microfluidics. Most often, when studying cells in suspensions, cells are trapped using flow and mechanical obstacles (Wheeler et al., Analytical Chemistry, 2003, 75, 3581-3586; Li and Li, Analytical Chemistry, 2005, 77, 4315-4322; Yang et al., Analytical Chemistry, 2002, 74, 3991-4001), centrifugation (Li et al., Lab on a Chip, 2004, 4, 174-180), dielectrophoresis (Seger et al., Lab on a Chip, 2004, 4, 148-151; Voldman et al., Biophysical Journal, 2001, 80, 531-541), or laser beams (Arai et al., Electrophoresis, 2001, 22, 283-288), and the soluble stimulus brought to the cells by convective flow. Alternatively, suspended cells are contained in a no-flow environment (Irimia et al., Analytical Chemistry, 2004, 76, 6137-6143), and solutions brought to cells by diffusion from short distances. The use of co-axial compartments in the microstructured approach accomplished two performances unmatched by any other current techniques. Uniform stimulation of cells along their circumference was for the first time possible and may become a useful tool for studying the response of cells to temporal stimuli in the absence of spatial gradients. Additionally, precise temporal control of sequential stimuli was possible through a single actuation. The temporal profile and sequence of stimulation can be adjusted by changing the size of the ring compartment and the size of the barriers, which once incorporated into the physical device, could assure reproducibility of experiments in the absence of sophisticated equipment.

In the above examples we demonstrated a new concept of microstructured membrane for the control of eukaryotic cells and fluid displacement in networks of microfluidic channels. Cell position and displacement in channels of high aspect ratios can be precisely controlled by reversible decoupling of cell and fluid movement using the microstructured membranes. Throughout the handling processes, cells were maintained in the same focal plane, allowing for easy observation using microscopy. Moreover, one unique feature of the microstructured membrane was the integration of multiple features on the same membrane with the possibility for simultaneous or sequential displacement, enabling complex actuation schemes with limited number of controls.

The microstructured membrane allowed the control of channels of any cross-section. High aspect ratios of 2:1 (height to width) or larger could easily be achieved, limited only by the SU8 photopatterning process or application requirements. For comparison, other PDMS valves are dependent on a rounded cross section of the channel (Unger et al., Science, 2000, 288, 113-116; Grover et al., Sensors and Actuators B-Chemical, 2003, 89, 315-323; Studer et al., Journal of Applied Physics, 2004, 95, 393-398; Weibel et al., Analytical Chemistry, 2005, 77, 4726-4733), and they can control channels with aspect ratios from 1:10, when fabricated using positive resist reflow (Unger et al., Science, 2000, 288, 113-116), to 1:1 when etched in a glass substrate (Grover et al., Sensors and Actuators B-Chemical, 2003, 89, 315-323). A valve with lateral actuation on a rectangular cross-section channels has been demonstrated, although only partial closure of the channels was possible (Sundararajan et al., Lab on a Chip, 2005, 5, 350-354). The direct consequence of the controlled channel geometric features was the easy control of suspensions of mammalian cells. While the rounded cross section works well for manipulating fluids and even small size (few microns) particles (like bacteria), it is not appropriate for handling eukaryotic cells having average sizes between 10 and 20 µm. Such large cells would not use the entire cross section of the channel or worse, are trapped at the acute angles at the edge of the rounded channels.

The microstructured membrane could seal a channel in the absence of the actuation pressure, only by elasticity of the membrane pressing against the valve seat, a feature shared with the three-layers PDMS valves (Grover et al., Sensors and Actuators B-Chemical, 2003, 89, 315-323; Li et al., Electrophoresis, 2005, 26, 3758-3764; Hosokawa and Maeda, Journal of Micromechanics and Microengineering, 2000, 10, 415-420). In contrast, most of the other elastomeric mechanical valves would seal upon the application of pressure through a thin membrane, and may introduce the challenge of maintaining the homeostasis of a cell suspension in the controlled channel. Gasses can diffuse easily through the membrane under the actuation pressure (Leclerc et al., Biotechnology Progress, 2004, 20, 750-755) and either diffuse in the cell suspension or form gas bubbles that can damage the cells. While a common solution for this problem is the filling of the control channels with liquid, recent results reported that the PDMS is permeable even to some commonly used liquids (Randall and Doyle, Proceedings of the National Academy of Sciences of the United States of America, 2005, 102, 10813-10818), and raise the concern of maintaining the homeostasis of the medium around cells during pressure actuation. Such potential shortcomings are avoided by the vacuum actuation of the microstructured membranes. Due to the elasticity of the PDMS, the microstructured membrane presses the microstructure against the valve seat and keeps the valve normally closed in the absence of actuation. The pressure that a valve could withstand without supplementary pressure in the control chamber was relatively low, in the range of few Pascals, but comparable to the pressures likely to drive very slow movement of cell suspensions.

Of practical importance is the unitary fabrication procedure, which allows the microstructured valve to be fabricated using soft lithography techniques based only on epoxy photoresists (e.g. SU8). However, the fabrication of a normally closed valve posed one significant challenge, namely how to selectively seal two distinct PDMS structures and simultaneously avoid having the valve become sealed during the bonding of the network layer. Previous technical solutions used mechanically clamping a PDMS membrane between the two glasses (Grover et al., Sensors and Actuators B-Chemical, 2003, 89, 315-323), partial bonding in combination with mechanical sticking (Li et al., Electrophoresis, 2005, 26, 3758-3764), or a water-soluble retardant (Baek et al., Journal of Micromechanics and Microengineering, 2005, 15, 1015-1020) for patterned PDMS bonding. In our approach, the patterned control of bonding was achieved by the patterning of a metal layer at the site of the valve seat. The thin layer of metal on the glass was then aligned to the valve seat and prevents the bonding of the PDMS to glass after exposure to oxygen plasma. The metal layer could eventually be etched at the end of the fabrication process resulting in fully transparent devices.

The unitary fabrication procedure is also important in reducing the costs associated with the fabrication of these devices. While for certain experiments the devices can be cleaned with various solutions and reused, in applications involving human blood or human cells, safety issues require these devices to be single use. Nonetheless, when translating the design into different materials, the implementation of unitary fabrication procedures becomes less challenging, ultimately resulting in cheaper, disposable devices.

OTHER EMBODIMENTS

All publications, patents, and patent applications mentioned in the above specification are hereby incorporated by reference. Various modifications and variations of the described method and system of the invention will be apparent to those skilled in the art without departing from the scope and spirit of the invention. Although the invention has been described in connection with specific embodiments, it should be understood that the invention as claimed should not be unduly limited to such specific embodiments. Indeed, various modifications of the described modes for carrying out the invention that are obvious to those skilled in the art are intended to be within the scope of the invention.

Other embodiments are in the claims.

What is claimed is:

1. A microfluidic device comprising first and second chambers sealable by contact between a base member and a mobile diaphragm comprising microstructures, wherein actuation of said mobile diaphragm allows eukaryotic cells in said first chamber to move to said second chamber, and prior to said actuation eukaryotic cells in said first chamber cannot move to said second chamber.

2. The device of claim 1, wherein said first chamber houses said eukaryotic cells.

3. The device of claim 1, wherein said second chamber houses a chemical stimulus for said eukaryotic cells.

* * * * *

UNITED STATES PATENT AND TRADEMARK OFFICE
CERTIFICATE OF CORRECTION

PATENT NO. : 8,343,756 B2
APPLICATION NO. : 12/089440
DATED : January 1, 2013
INVENTOR(S) : Mehmet Toner and Daniel Irimia It is certified that error appears in the above-identified patent and that said Letters Patent is hereby corrected as shown below:

Page 10, Column 1, Line 3, insert -- This invention was made with Government support under Grant No(s). GM071345 awarded by the National Institutes of Health. The Government has certain rights in this invention. --.

Signed and Sealed this
Seventh Day of May, 2013

Teresa Stanek Rea
*Acting Director of the United States Patent and Trademark Office*